(12) United States Patent
Matsumura

(10) Patent No.: US 10,925,584 B2
(45) Date of Patent: Feb. 23, 2021

(54) TGC CONTROLS FOR AN ULTRASONIC DIAGNOSTIC IMAGING SYSTEM

(71) Applicant: KONINKLIJKE PHILIPS N.V., Eindhoven (NL)

(72) Inventor: Towa Matsumura, Worcester, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 391 days.

(21) Appl. No.: 15/855,098

(22) Filed: Dec. 27, 2017

(65) Prior Publication Data

US 2018/0116637 A1 May 3, 2018

Related U.S. Application Data

(63) Continuation of application No. 15/022,392, filed as application No. PCT/IB2014/064360 on Sep. 10, 2014, now Pat. No. 9,861,343.

(60) Provisional application No. 61/879,781, filed on Sep. 19, 2013.

(51) Int. Cl.
| | | |
|---|---|---|
| *A61B 8/14* | (2006.01) |
| *A61B 8/00* | (2006.01) |
| *G01S 7/52* | (2006.01) |
| *F21V 33/00* | (2006.01) |
| *G01S 15/89* | (2006.01) |
| *F21Y 101/00* | (2016.01) |
| *A61B 90/30* | (2016.01) |

(52) U.S. Cl.
CPC ............... *A61B 8/54* (2013.01); *A61B 8/14* (2013.01); *A61B 8/467* (2013.01); *F21V 33/0068* (2013.01); *G01S 7/52033* (2013.01); *A61B 8/461* (2013.01); *A61B 2090/309* (2016.02); *F21Y 2101/00* (2013.01); *G01S 15/8925* (2013.01)

(58) Field of Classification Search
CPC ..... A61B 2090/309; A61B 8/14; A61B 8/461; A61B 8/467; A61B 8/54; F21V 23/003; F21V 33/0068; G01S 15/8925; G01S 7/52033
See application file for complete search history.

(56) References Cited

U.S. PATENT DOCUMENTS

| | | | |
|---|---|---|---|
| 4,914,673 A * | 4/1990 | Imura | G01J 5/08 250/351 |
| 5,482,045 A | 1/1996 | Rust et al. | |
| 5,997,479 A | 12/1999 | Savord et al. | |
| 6,436,048 B1 | 8/2002 | Pesque | |

(Continued)

FOREIGN PATENT DOCUMENTS

| | | |
|---|---|---|
| JP | 63197438 | 8/1988 |
| JP | 2009078083 A | 4/2009 |

(Continued)

*Primary Examiner* — Mark D Remaly

(57) ABSTRACT

The TGC slide switches which provide the TGC control of an ultrasonic diagnostic imaging system have LEDs mounted on the sliders of the slide switches so that the switches can be easily visualized in a darkened room. The light emitted by the LED of a switch is changed to an indicative color or brightness when the slider of the switch is set in its default position for the application of a nominal gain to echo signals received from a given depth.

15 Claims, 4 Drawing Sheets

(56) References Cited

U.S. PATENT DOCUMENTS

| | | |
|---|---|---|
| 2003/0187353 A1 | 10/2003 | Ng |
| 2006/0112033 A1 | 5/2006 | Vion |
| 2007/0230759 A1 | 10/2007 | Tamura |
| 2009/0069682 A1 | 3/2009 | Hastings |
| 2011/0054317 A1 | 3/2011 | Lin |
| 2012/0044277 A1* | 2/2012 | Adachi ............... G09G 3/3426 345/690 |
| 2013/0096575 A1 | 4/2013 | Olson |

FOREIGN PATENT DOCUMENTS

| | | |
|---|---|---|
| JP | 2012061239 A1 | 3/2012 |
| RU | 2125836 C1 | 2/1999 |

* cited by examiner

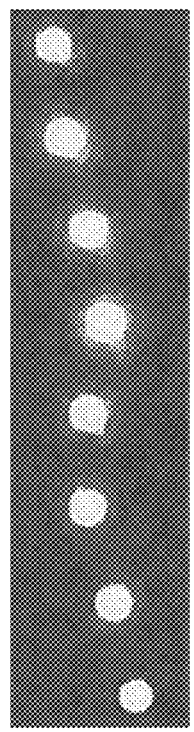
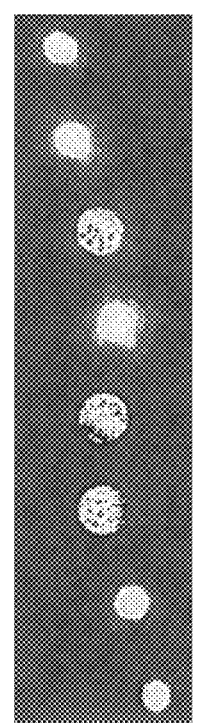
FIG. 4a    FIG. 4b
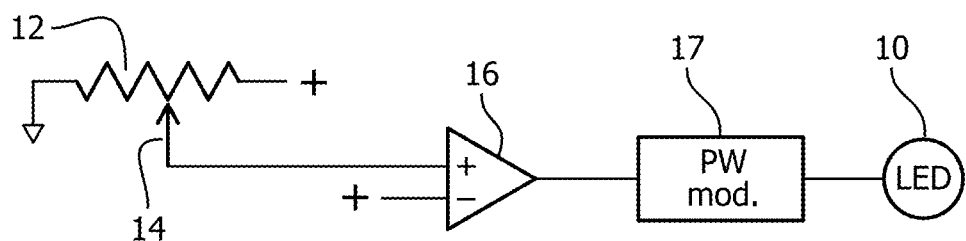
FIG. 5a
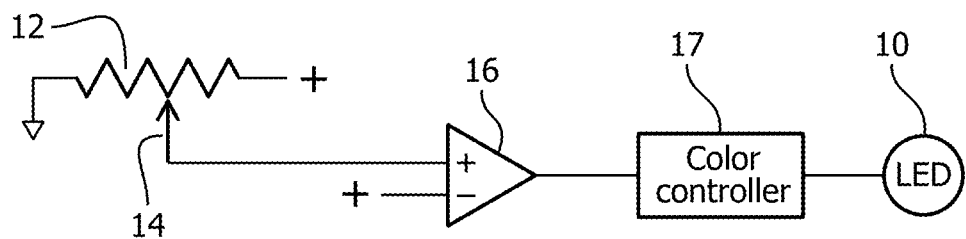
FIG. 5b

TGC CONTROLS FOR AN ULTRASONIC DIAGNOSTIC IMAGING SYSTEM

The present application is a continuation of U.S. patent application Ser. No. 15/022,392 filed Mar. 16, 2016, which is the U.S. National Phase application under 35 U.S.C. § 371 of International Application No. PCT/IB2014/064360, filed Sep. 10, 2014, which claims the benefit of U.S. Provisional Application Ser. No. 61/879,781 filed Sep. 19, 2013. These applications are hereby incorporated by reference herein.

This invention relates to medical diagnostic ultrasound systems and, in particular, to ultrasound systems with controls for time gain compensation of received ultrasonic echo signals.

When ultrasound signals are transmitted into the body by an ultrasound imaging probe, the waves are continuously attenuated during their passage through tissue, and the returning echoes are further attenuated as they travel back to the transducer. As a consequence echoes are increasingly attenuated as a function of the depth in the body from which they return. The time-honored solution to this attenuation problem is to amplify the received echo signals as a function of the time at which they are received: echoes returning later from the time of transmit are amplified more greatly than those received earlier from shallower depths. The circuitry which performs this amplification is known as time gain compensation (TGC) circuitry, also referred to as sensitivity time control (STC). But the relationship between time and attenuation is not a purely linear one. The echoes experience different degrees of attenuation depending upon the tissue through which they travel. For instance, when imaging the heart relatively little attenuation is experienced as echoes travel through the blood in the heart chamber, and greater attenuation is experienced as echoes travel through the heart muscle, the myocardium. Accordingly the controls for TGC are a series of switches which affect the gain applied at different depths over the depth of the ultrasound image. Typically the switches are slide switches arranged in a column on the ultrasound system control panel. The columnar orientation is immediately seen to correspond to successively greater depths of the image. The switches are generally slide switches with a center position which sets a nominal gain for the corresponding image depth. The slide switches can be moved laterally in either direction to apply more or less than the nominal gain at each depth. Thus the gain profile can be set nonlinearly to vary the gain in relation to the anatomical makeup of the region of the body being imaged. In modern ultrasound systems gain profiles can be stored for particular imaging applications and recalled, applied, and adjusted by the slide switches as appropriate to produce an image of uniform brightness and grey shades over the depth of the image as described in U.S. Pat. No. 5,482,045 (Rust et al.)

Ultrasound exams are often performed in a darkened room so that the sonographer can most easily discern the appearance of the images and subtle structures and functions (e.g., blood flow) being images. To enable the sonographer to readily see the controls of the system control panel, the control are often back-lit to aid visibility. The TGC controls can be lighted in various ways. But even with effective back-lighting, the sonographer is often not able to distinguish the specific positions of the TGC switches. In particular, it is frequently difficult for the sonographer to see whether the TGC switches are still set in their nominal center positions or have been adjusted to a different gain setting. Accordingly it is desirable to provide TGC controls which are easily discernible and their setting readily visualized in a darkened exam room.

In accordance with the principles of the present invention, a diagnostic ultrasound system is described with illumination provided for the individual switches of the TCG control. The illumination is uniquely controlled or modulated when a switch is in its center position as by color or brightness modulation or control. The sonographer is thereby readily able to visualize the gain setting of the switches from their orientation pattern and to immediately discern those switches which are set in their nominal center positions.

In the drawings:

FIGS. 4a and 4b illustrate illuminated TGC controls of the present invention when viewed in a darkened room.

FIGS. 5a and 5b illustrate implementations of the present invention by pulse width modulation and color control of an LED on a TGC control.

Figure 1:
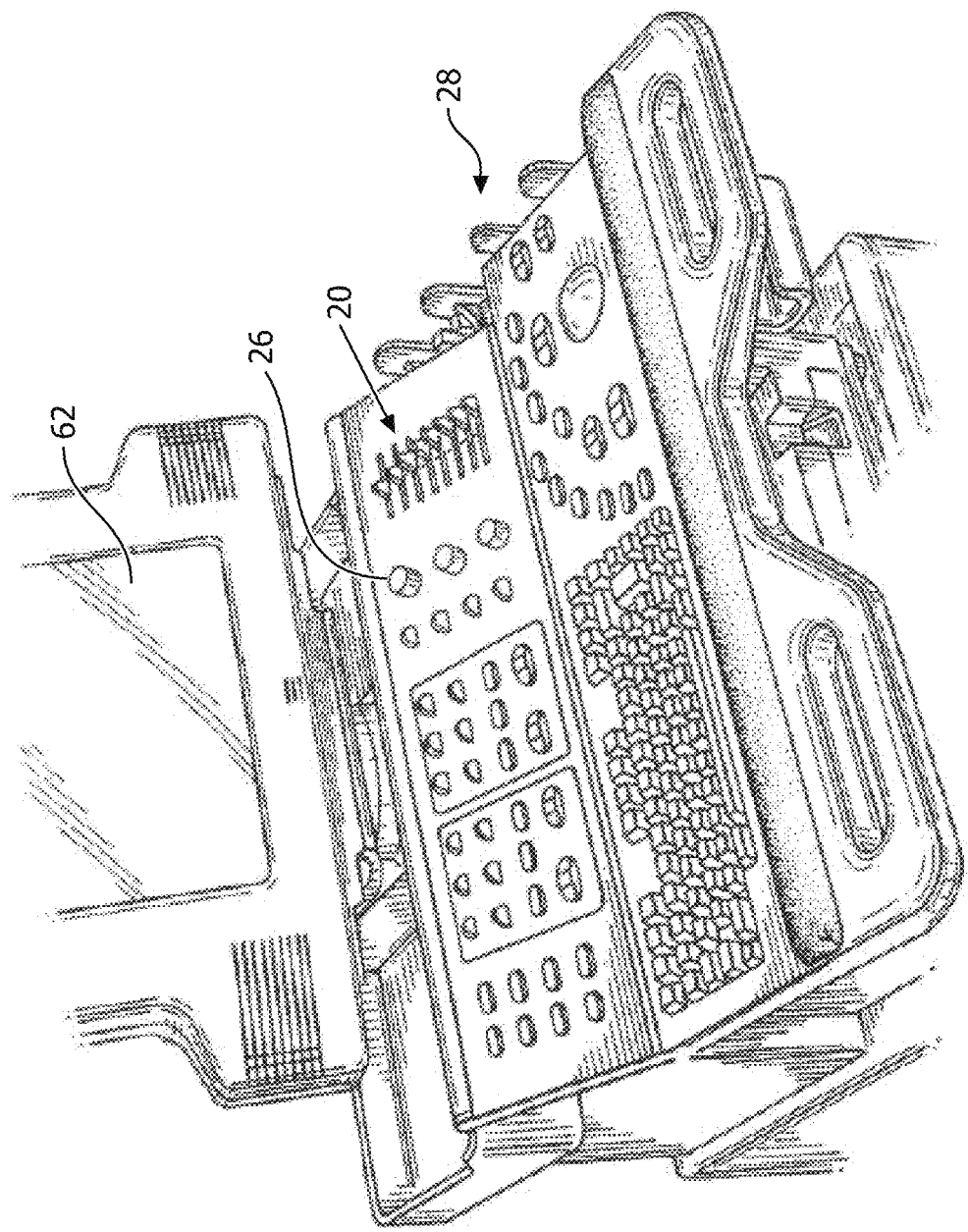
FIG. 1 illustrates the control panel of an ultrasonic diagnostic imaging system.

Referring first to FIG. 1, an ultrasound system control panel 28 is shown in a perspective view. When a user desires to perform a particular ultrasonic examination such as imaging the liver, the user selects the desired procedure by using the controls on the control panel 28. This may involve interaction with a menu of parameters and performance choices shown on the display monitor 62 using the trackball and a select button on the control panel to select the desired parameters. Upon selection of an imaging procedure the system will select an optimal TGC characteristic stored in the system memory for the procedure and apply it to the TGC circuitry as described below. The TGC circuitry will then control the gain of the TGC amplifier in the system's signal path in accordance with this optimal TGC characteristic. The system will also supply graphical information to the image display so that a visual representation of the optimal TGC characteristic will be shown on the image display 62 adjacent to the image. This TGC curve then illustrates the relative amounts of gain applied to echoes returning from progressively deeper depth of the image region.

Figure 2:
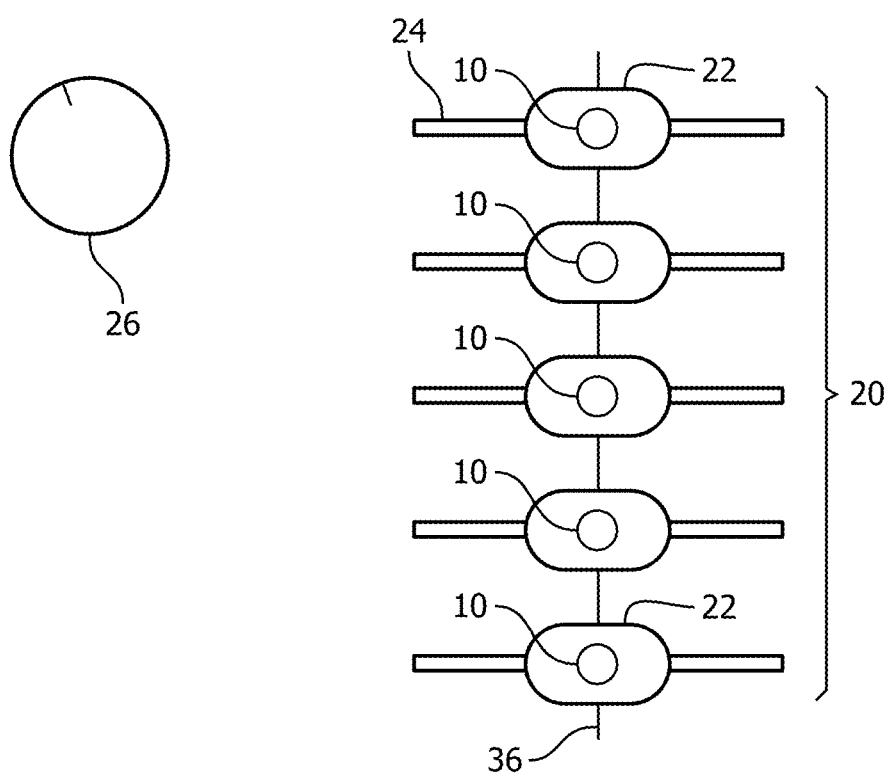
FIG. 2 is a detailed view of the TGC control of the ultrasound system of FIG. 1 constructed in accordance with the principles of the present invention.

The optimal, predetermined TGC characteristic will be displayed and used to control the amplifier of the TGC circuitry when the slide switches 20 on the control panel are vertically aligned in their central position 36 as shown in FIG. 2. If the clinician finds that variation from the predetermined characteristic is needed to better image a particular patient, the clinician will move the slide switches to the right or left to reset the slope segments of the TGC gain characteristic. As the switches are moved the changes are communicated from the control panel 28 to the TGC circuitry, which applies the incremental changes to the predetermined characteristic. The effects of these changes are shown by visual changes to the displayed TGC characteristic on the display screen. When the clinician is finished adjusting the TGC switches 20 the variation from the predetermined characteristic is indicated by the new physical positions of the switches on the control panel and the final TGC characteristic is shown on the display screen. A uniform gain adjustment over the full image depth is applied by adjusting a gain control adjustment 26.

Figure 3:
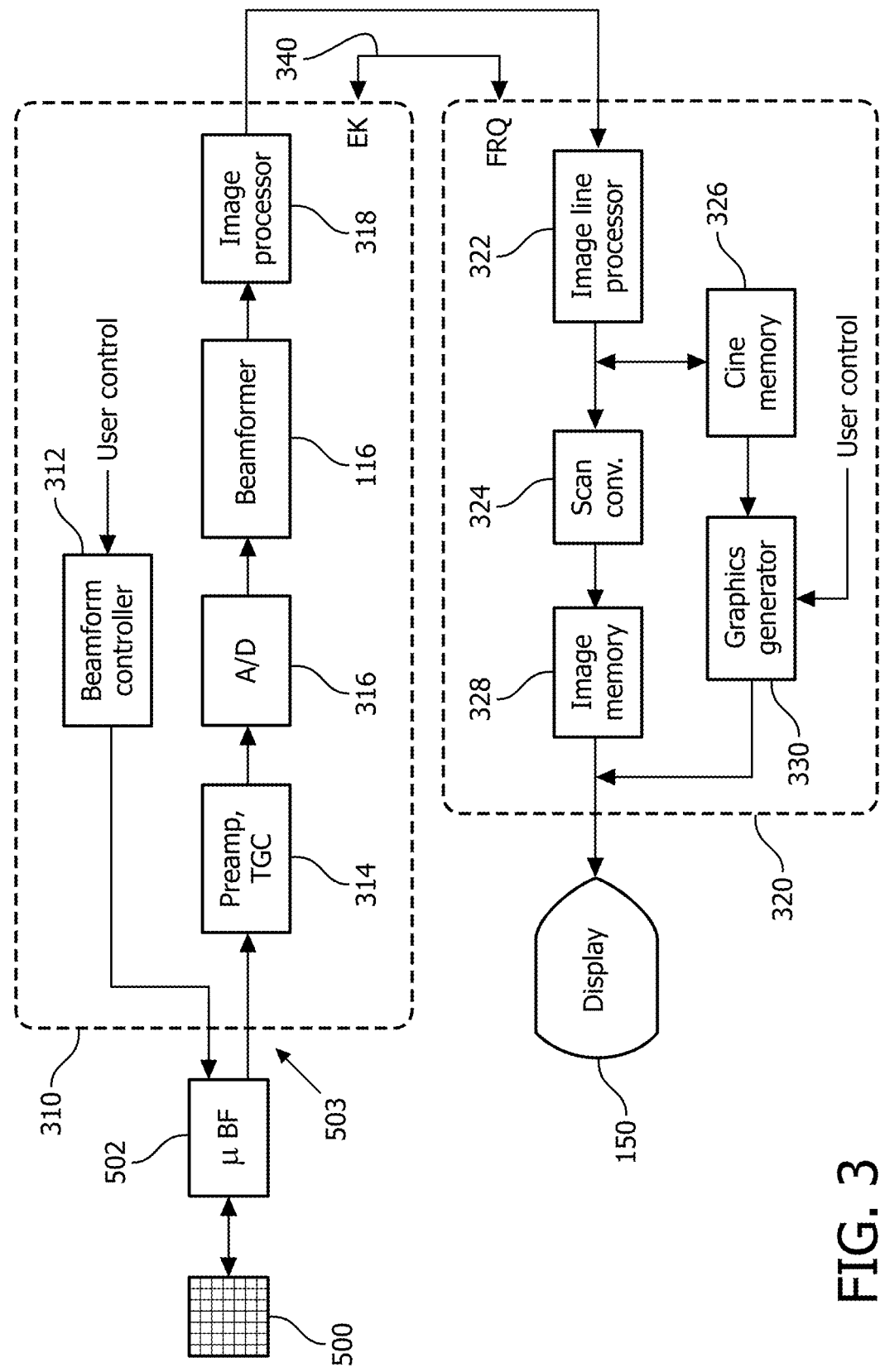
FIG. 3 illustrates in block diagram form the major components of an ultrasound system including TGC circuitry.

Referring to FIG. 3, an ultrasound system constructed in accordance with the principles of the present invention is shown in block diagram form. In this implementation the ultrasound probe includes a two dimensional array transducer 500 and a microbeamformer 502. The present invention may be used with probes employing either one dimensional or two dimensional transducer arrays. The microbeamformer contains circuitry which controls the signals applied to groups of elements ("patches") of the array transducer 500 and does some combining of the echo signals received by elements of each group. Micro-beamforming in the probe advantageously reduces the number of conductors in the cable 503 between the probe and the ultrasound system and is described in U.S. Pat. No. 5,997,479 (Savord et al.) and in U.S. Pat. No. 6,436,048 (Pesque).

The probe is coupled to the scanner 310 of the ultrasound system. The scanner includes a beamform controller 312 which is responsive to a user control on the control panel, such as a probe select control, and provides control signals to the microbeamformer 502 instructing the probe as to the timing, frequency, direction and focusing of transmit beams for the desired image and the selected probe. The beamform controller also control the beamforming of received echo signals by its coupling to the analog-to-digital (A/D) converters 316 and a beamformer 116. Echo signals received by the probe are amplified by preamplifier and an amplifier of the TGC (time gain control) circuitry 314, then digitized by the A/D converters 316. The digitized echo signals are then formed into beams by the beamformer 116. The echo signals from individual elements or patches of elements of the array 500 are then processed by an image processor 318 which performs digital filtering, B mode detection, and/or Doppler processing, and can also perform other signal processing such as harmonic separation, speckle reduction through frequency compounding, digital gain (including digital TGC) and other desired image or signal processing.

The echo signals produced by the scanner 310 are coupled to a display subsystem 320 which processes the echo signals for display in the desired image format. The echo signals are processed by an image line processor 322 which is capable of sampling the echo signals, splicing segments of beams into complete line signals, and averaging line signals for signal-to-noise improvement or flow persistence. The image lines of each image are scan converted into the desired image format by a scan converter 324 which performs R-theta conversion as is known in the art. The images are then stored in an image memory 328 from which they can be displayed on the display 150. The images in memory are also overlayed with graphics to be displayed with the images, such as the TGC characteristic described above, which are generated by a graphics generator 330 which is responsive to a user control. Individual image frames or image frame sequences can be stored in a cine memory 326 during capture of image loops.

In accordance with the principles of the present invention, each slider switch 22 of the TGC controls is lighted with an LED 10 mounted on the slider of the switch as shown in FIG. 2. Each slider has a range of control dictated by the extent of a cutout 24 in the control panel along which the slider can travel laterally. Thus, if the uppermost slider (corresponding to the shallowest depth) is moved to the left it will appear to the left of the column of the LEDs of the other switches. The sonographer can see at a glance that at the shallowest depth a low gain setting is in place, while the gains applied at the deeper depths are all nominal gain settings. The illuminated LEDs on the switch sliders will make this visibly clear even in a darkened room.

In accordance with a further aspect of the present invention, each LED 10 produces a distinguishing illumination when it is set in its nominal central position 36. A variety of different illumination differentiation techniques may be used. One is to illuminate the LED brightly when the slider 22 is in its center position, and dimmer when the slider is moved away from the center position. FIG. 5a illustrates a potentiometer 12 of a TGC slider switch with a slider arm 14. When the slider is centered, the differential amplifier 16 switches to a low output, which disables the input of a pulse width modulator 17. In this null state, the LED 10 is driven by a steady voltage, producing a bright illumination. But when the slider arm 14 is moved off center, the differential amplifier 16 switches to a high output, enabling the pulse width modulator 17, which drives the LED 10 with a pulse width modulated pulse train. The LED illumination is then dimmer.

Another approach to illumination variation is to vary the color of the light of the LED when the slider 22 is in its center position. In FIG. 5b when the slider arm 14 is centered the differential amplifier 16 causes the LED to be illuminated with a predetermined color such as red. This can be done with a color controller 17 that selects the color of an RGB LED, or by varying the color temperature of the LED 10. When the slider arm is moved off center, the color controller 17 selects a different color for an RGB LED, white instead of red, for instance, or changes the color temperature to a different one than used in the centered position.

Each TGC control will produce a value (digital or analog) depending upon its setting, which is coupled to an illumination controller. The illumination controller compares the digital value against the known value of the center position setting. If the two values are not equal the difference value is used to control the pulse width modulation duty cycle and/or frequency to dim the illumination. For the color modulation implementation three independent pule width modulators are used to control the duty cycle or frequency of each color of an RGB LED to produce virtually any desired color.

FIGS. 4a and 4b illustrate the effect of such color modulation. FIG. 4a illustrates a series of lights on eight TGC sliders. The settings range from a low gain at the shallow depths by the top sliders, which are set to the left of center, and ranging down to greater than nominal gains at the deepest depths where it is seen that the lower-most sliders have been moved to the right. This curved pattern of white LEDs gives little indication of which sliders were untouched and remain in their nominal gain positions. But in the example of FIG. 4b, the LEDs for the third, fifth, and sixth sliders 26, 27, and 28 are modulated to produce a reddish color (as represented by the dotted patterns), which clearly stand out in relation to the other white LEDs. The sonographer can see at a glance that no adjustment has been made to the nominal gains at these depths.

Other illumination schemes will readily occur to those skilled in the art. The LEDs could be illuminated red when moved to a higher gain setting (to the right), green when moved to a lower gain setting (to the left), and white when set in the nominal center position, for instance. Another alternative is to use the pulse width modulator to blink the LEDs on and off to indicate by the blinking those that are in the center position or those that have been moved.

What is claimed is:

1. An ultrasound system with gain compensation, comprising:
   a control panel comprising at least one gain compensation control, wherein the at least one gain compensation control is configured to be set in a nominal central position or adjusted to other positions to control gain compensation;
a lighting device adapted to provide a visible indication to a user when the at least one gain compensation control is set in the nominal central position; and
an illumination controller, coupled to the lighting device, that is responsive to a position of the at least one gain compensation control, wherein the illumination controller is configured to generate visibly distinguishing illumination when the at least one gain compensation control is set in the nominal central position as compared to when the at least one gain compensation control is set in other positions.

2. The ultrasound system of claim 1, wherein the at least one gain compensation control comprises a slider.

3. The ultrasound system of claim 2, wherein the slider can be moved along a lateral range of adjustment, and wherein the nominal central position is a center of the lateral range.

4. The ultrasound system of claim 3, comprising a slider position sensor that is responsive to movement of the slider along its range of adjustment and is configured to sense when the slider is in the center of the lateral range.

5. The ultrasound system of claim 4, wherein the illumination controller is further responsive to the slider position sensor.

6. The ultrasound system of claim 5, wherein the slider position sensor further comprises a differential amplifier.

7. The ultrasound system of claim 1, wherein the illumination controller is configured to generate the visibly distinguish illumination by changing a color of light.

8. The ultrasound system of claim 1, wherein the illumination controller is configured to generate the visibly distinguish illumination changing a brightness of light.

9. The ultrasound system of claim 1, wherein the at least one gain compensation control comprises a time compensation control.

10. The ultrasound system of claim 1, wherein the illumination controller further comprises a pulse width modulator.

11. The ultrasound system of claim 1, wherein the lighting device comprises a light emitting diode (LED).

12. The ultrasound system of claim 10, wherein the pulse width modulator is configured to drive the lighting device with a width-modulated pulse to reduce the brightness of light produced by the lighting device.

13. The ultrasound system of claim 7, wherein the color of light comprises a reddish color when the gain compensation control is set in its nominal central position.

14. The ultrasound system of claim 1, wherein the lighting device comprises an RGB LED, and wherein the illumination controller comprises an LED color controller.

15. The ultrasound system of claim 1, wherein the gain compensation control is configured to control time gain compensation by enabling user adjustment of the amplification applied to ultrasonic echo signals received from different depths of imaging.

* * * * *